(12) United States Patent
Ho et al.

(10) Patent No.: US 11,207,430 B2
(45) Date of Patent: Dec. 28, 2021

(54) GADOLINIUM EXPRESSED LIPID NANOPARTICLES FOR MAGNETIC RESONANCE IMAGING

(71) Applicant: University of Washington, Seattle, WA (US)

(72) Inventors: Rodney J. Y. Ho, Mercer Island, WA (US); John D. Hoekman, Seattle, WA (US); Ken Maravilla, Bellevue, WA (US)

(73) Assignee: University of Washington, Seattle, WA (US)

( * ) Notice: Subject to any disclaimer, the term of this patent is extended or adjusted under 35 U.S.C. 154(b) by 292 days.

(21) Appl. No.: 15/369,661

(22) Filed: Dec. 5, 2016

(65) Prior Publication Data

US 2017/0173190 A1 Jun. 22, 2017

Related U.S. Application Data

(63) Continuation of application No. 13/208,100, filed on Aug. 11, 2011, now abandoned, which is a continuation of application No. PCT/US2010/024324, filed on Feb. 16, 2010.

(60) Provisional application No. 61/152,459, filed on Feb. 13, 2009, provisional application No. 61/162,989, filed on Mar. 24, 2009.

(51) Int. Cl.
*A61K 49/18* (2006.01)
*A61P 35/00* (2006.01)
*A61K 49/08* (2006.01)
*A61K 51/04* (2006.01)
*A61K 51/12* (2006.01)
*B82Y 5/00* (2011.01)

(52) U.S. Cl.
CPC ........ *A61K 49/1824* (2013.01); *A61K 49/085* (2013.01); *A61K 49/1806* (2013.01); *A61K 49/1812* (2013.01); *A61K 49/1881* (2013.01); *A61K 51/0408* (2013.01); *A61K 51/0497* (2013.01); *A61K 51/1227* (2013.01); *B82Y 5/00* (2013.01)

(58) Field of Classification Search
None
See application file for complete search history.

(56) References Cited

U.S. PATENT DOCUMENTS

| | | |
|---|---|---|
| 2002/0168321 A1 | 11/2002 | Tournier et al. |
| 2003/0082103 A1 | 5/2003 | Wartchow |
| 2005/0112065 A1 | 5/2005 | Drummond |
| 2005/0265922 A1 | 12/2005 | Nie et al. |
| 2007/0275048 A1 | 11/2007 | Liu |
| 2011/0104261 A1 | 5/2011 | Drummond et al. |

FOREIGN PATENT DOCUMENTS

| | | |
|---|---|---|
| JP | 10-504044 A | 4/1998 |
| JP | 2007-515471 A | 6/2007 |
| JP | 2007-528854 A | 10/2007 |
| WO | 97/00087 A1 | 1/1997 |
| WO | 2004/083902 A3 | 9/2004 |
| WO | 2005/063306 A1 | 7/2005 |
| WO | 2006/064451 A2 | 6/2006 |
| WO | 2008/109712 A2 | 9/2008 |
| WO | 2008/130137 A1 | 10/2008 |
| WO | 2009/110939 A2 | 9/2009 |

OTHER PUBLICATIONS

Extended European Search Report dated Apr. 9, 2015, issued in corresponding European Patent Application No. 10741884.0, filed Feb. 16, 2010, 8 pages.
First Office Action, dated Oct. 11, 2016, issued in corresponding Japanese Application No. 2015-229868, 4 pages.
Frullano, L., and T.J. Meade, "Multimodal MRI Contrast Agents," Journal of Biological Inorganic Chemistry 12(7):939-949, Jul. 2007.
Hak, S., et al., "A High Relaxivity Gd(III)DOTA-DSPE-Based Liposomal Contrast Agent for Magnetic Resonance Imaging," European Journal of Pharmaceutics and Biopharmaceutics 72(2):397-404, Jun. 2009.
Hamoudeh, M., et al., "Radionuclides Delivery Systems for Nuclear Imaging and Radiotherapy of Cancer," Advanced Drug Delivery Reviews 60(12):1329-1346, Sep. 2008.
International Search Report and Written Opinion dated Nov. 11, 2010, issued in corresponding International Application No. PCT/US2010/024324, filed Feb. 16, 2010, 10 pages.
Japanese Office Action dated Apr. 8, 2014, issued in corresponding Japanese Application No. 2011-550316, filed Feb. 16, 2010, 7 pages.
Mulder, W.J.M., "Lipid-Based Nanoparticles for Magnetic Resonance Molecular Imaging: Design, Characterization, and Application," doctoral dissertation, Eindhoven Technische Universiteit, Eindhoven, Netherlands, 2006, 185 pages.
Mulder, W.J., et al., "MR Visualization of Neovascularization in Advanced Atherosclerotic Plaques Using Targeted Paramagnetic and Fluorescent Micelles," Proceedings of the International Society for Magnetic Resonance Medicine, May 19-25, 2007, Berlin, p. 2465.

(Continued)

*Primary Examiner* — Tigabu Kassa
(74) *Attorney, Agent, or Firm* — Christensen O'Connor Johnson Kindness PLLC (57) ABSTRACT

Lipid nanoparticles expressing metal ions and methods for using the compositions for magnetic resonance imaging.

7 Claims, 11 Drawing Sheets

(56) References Cited

OTHER PUBLICATIONS

Mulder, W.J.M., et al., "A Liposomal System for Contrast-Enhanced Magnetic Resonance Imaging of Molecular Targets," Bioconjugate Chemistry 15(4):799-806, Jun. 2004.
Notification of Reexamination dated Feb. 1, 2016, issued in corresponding Chinese Application No. 201080010560.5, filed Feb. 16, 2010, 38 pages.
Rofsky, N.M., et al., "Nephrogenic Systemic Fibrosis: A Chemical Perspective," Radiology 247(3):608-612, Jun. 2009.
Sandström, M.C., et al., "Structure of Mixed Micelles Formed in PEG-Lipid/Lipid Dispersions," Langmuir 23(8):4192-4198, Apr. 2007.
Torchilin, V.P., "PEG-Based Micelles as Carriers of Contrast Agents for Different Imaging Modalities," Advanced Drug Delivery Reviews 54(2):235-252, Feb. 2002.
Tournier, H., et al., "Gadolinium-Containing Mixed Micelle Formulations: A New Class of Blood Pool MRI/MRA Contrast Agents," Academic Radiology 9(Suppl. 1):S20-S28, May 2002.
Trubetskoy, V.S., and V.P. Torchilin, "Polyethyleneglycol Based Micelles as Carriers of Therapeutic and Diagnostic Agents," S.T.P. Pharma Sciences 6(1):79-86, Jan. 1996.
Van Schooneveld, M.M., et al., "Improved Biocompatibility and Pharmacokinetics of Silica Nanoparticles by Means of a Lipid Coating: A Multimodality Investigation," Nano Letters 8(8):2517-2525, Aug. 2008.
Office Action (EPC) dated May 8, 2017, issued in corresponding European Application No. 10741884.0, filed Feb. 16, 2010, 5 pages.
Notification of Office Action dated Feb. 28, 2019, issued in corresponding Chinese Application No. 201610996986.1, filed Feb. 16, 2010, 19 pages.

Pre-contrast　　20 min　　　6 hr　　　24 hr
FIG. 3A.　FIG. 3B.　FIG. 3C.　FIG. 3D.

GADOLINIUM EXPRESSED LIPID NANOPARTICLES FOR MAGNETIC RESONANCE IMAGING

CROSS-REFERENCES TO RELATED APPLICATIONS

This application is a continuation of U.S. application Ser. No. 13/208,100, filed Aug. 11, 2011, which is a continuation of International Application No. PCT/US2010/024324, filed Feb. 16, 2010, which application claims the benefit of U.S. Provisional Application No. 61/152,459, filed Feb. 13, 2009, and U.S. Provisional Application No. 61/162,989, filed Mar. 24, 2009. Each application is incorporated herein by reference in its entirety.

STATEMENT OF GOVERNMENT LICENSE RIGHTS

This invention was made with Government support under Grant Nos. AI 077390 and AI 052663 awarded by the National Institutes of Health. The Government has certain rights in the invention.

BACKGROUND OF THE INVENTION

Early diagnosis of lymph node involvement is essential to determine treatment for most types of cancer. Lymphadenectomy and histological evaluation is currently the gold standard, but is not ideal because it is invasive and can produce false negatives. Magnetic resonance (MR) imaging has become a powerful and non-invasive tool for detecting the spread of cancer to the lymph nodes. Standard MR imaging relies on size and morphology criteria to determine occult lymphoid tissues including lymph node metastasis, which has as low as 60% accuracy. MR contrast enhancing agents are becoming more widely used due to their usefulness in early tumor detection. Contrast enhancing agents diffuse into metastatic lymph nodes and healthy lymph nodes at different rates causing "filling defects." Predicting lymph node metastasis using filling defects from contrast agents as opposed to size criteria can increase the sensitivity from 29% to 93%.

Generally, there are two types of MR contrast enhancing agents. Superparamagnetic contrast agents have a low r2/r1 ratio and create dark spots in T2- and T2*-weighted images. These are usually based on iron oxide particles and are referred to as negative contrast agents. On the other hand, paramagnetic contrast agents increase the r1 relaxivity and have a high r2/r1 ratio, creating bright spots in T1 weighted MR images. These contrast agents are known as positive contrast agents and are usually complexes of gadolinium ($Gd^{3+}$).

T1 shortening comes about through dipole-dipole interactions with the protons in water so $Gd^{3+}$, with its seven unpaired electrons, is the optimal choice for a T1 relaxation agent. Because $Gd^{3+}$ is a heavy metal toxin, it is commonly delivered as a tightly bound linear or macroscopic chelate. Chelated forms of $Gd^{3+}$ reduce toxicity by preventing cellular uptake of free $Gd^{3+}$ and by limiting the clearance almost exclusively to renal filtration that resulted in renal toxicities. Despite reducing toxicity, the rapid clearance and small molecular size of gadolinium chelates mean that low levels of $Gd^{3+}$ accumulates in the lymph nodes, making these agents a poor choice for MR lymphography. In addition, the FDA posted a warning about the risk of serious nephrogenic systemic fibrosis for all commercially available gadolinium contrast agent to identify well-perfused tissues and organs in subjects with acute or chronic renal insufficiency.

Liposomes and lipid nanoparticles containing $Gd^{3+}$ have several advantages for MR contrast imaging of lymph nodes. Liposomes as well as lipid nanoparticles can lower the toxicity by encapsulating or binding to their surfaces a large amount of $Gd^{3+}$ However, the rapid clearance mechanism of intravenously (IV) administered liposomes does not significantly improve liposome-associated $Gd^{3+}$ accumulation in the lymph nodes. Only a fraction of the lipid nanoparticles in blood are phagocytosed by reticuloendothelial cells, and only a fraction of those cells traverse to lymphatic system. Thus, IV administered liposomes provide indirect targeting of the lymphatic system and lymph nodes. However, this approach results in a majority of $Gd^{3+}$ carrying liposomes eliminated through reticuloendothelial cells in blood. The pharmacokinetics of liposomes in blood can be optimized for lymph node accumulation through size and surface modification. Reducing the diameter of the liposomes below 200 nm decreases phagocytic dependent clearance and increases the circulation time in the blood. Adding polyethylene glycol (PEG, commonly referred to as PEGylation) to the liposome surface can also increase the circulation time and stability of liposomes.

Currently, gadolinium chelated with diethylenentriaminepentaacetyl (DTPA) provides contrast in magnetic resonance imaging to identify pathogenic tissues. Unfortunately, the soluble Gd-DTPA complexes approved for clinical use, such as OMNISCAN, are cleared within a few minutes and do not provide sufficient concentrations or time in lymphoid tissues. In addition, the residual fraction of gadolinium can lead to fibrosis in patients with renal insufficiency.

Despite the advances in the development of contrast agents, a need exists for improved contrast agents having longer in vivo life, provide sufficient concentration in tissues to be analyzed, and low residual gadolinium concentrations to avoid side effects. The present invention seeks to fulfill this need and provide further related advantages.

SUMMARY OF THE INVENTION

The present invention provides compositions expressing metal ions and methods for using the compositions.

In one aspect, the invention provides a composition, comprising a lipid, a polyalkylene-containing lipid, and a lipid-containing metal chelator.

Representative lipids include phospholipids, sphingolipids, cholesterol and steroid derivatives, bile acids and derivatives, cardilipin, acyl-glycerides and derivatives, glycolipids, acyl-peptides, fatty acids, carbohydrate-based polymers, functionalized silica, polyanhydride polymers, polylactate-glycolate polymers, and biopolymers. In one embodiment, the lipid is a phospholipid. Representative phospholipids include 1,2-distearoyl-sn-glycero-3-phosphocholine (DSPC); dipalmitoyl phosphatidylcholine; dimysristoyl phosphatidyl choline; dioleoyl phosphatidyl choline; trans-esterified phospholipids derived from eggs, soybean, flaxseed, and the like; and phosphatidylcholine substituted with phosphatidyl ethanolamine, phosphatidylglycerol, phosphatidyl serine, and phosphatidic acids.

Representative polyalkylene-containing lipids include polyoxyethylene-containing lipids or polyoxypropylene-containing lipids. In one embodiment, the polyalkylene-containing lipid is a phospholipid functionalized with polyethylene glycol such as N-(carbonylmethoxypolyethyleneglycol-2000)-1,2-distearoyl-sn-glycero-3-phosphoethanol-amine (mPEG-2000-DSPE).

Representative lipid-containing metal chelators include 1,2-distearoyl-sn-glycero-3-phosphoethanolamine-N-diethylenetriaminepentaacetyl (DSPE-DTPA), tetraazacyclodo-decane, tetraacety(gadodiamide)-PE, and lipid-functionalized-[N,N-bis[2-[bis(carboxymethyl)amino]-ethyl]-glycinato-(5")]. In one embodiment, the lipid-containing metal chelator comprises a PEGylated lipid moiety. In one embodiment, the lipid-containing metal chelator is a PEGylated DTPA. In other embodiments, the lipid-containing metal chelator is a DSPE-BOPTA, a DSPE-DO3A, and a DSPE-DOTA.

In one embodiment, the composition further includes a targeting moiety. Representative targeting moieties include proteins, polypeptides, peptides, antibodies or fragments thereof, small molecules, sugars or polysaccharides or derivatives thereof, and nucleic acids.

In one embodiment, the composition of the invention has the form of a nanoparticle. In one embodiment, the nanoparticle has a diameter of from about 5 nm to about 2 μm. In one embodiment, the nanoparticle has a diameter of from about 50 nm to about 100 μm.

The composition of the invention can further include a metal ion. Suitable metal ions include paramagnetic metal ions and ions of radio-isotopes. Representative paramagnetic metal ions include $Gd^{3+}$, $Cu^{2+}$, $Fe^{3+}$, $Fe^{2+}$, and $Mn^{2+}$ ions. Representative ions of radio-isotopes include $^{68}Ga$, $^{55}Co$, $^{86}Y$, $^{90}Y$, $^{177}Lu$, and $^{111}In$ ions.

In another aspect, the invention provides administrable compositions including a carrier and a plurality of the nanoparticles of the invention. Suitable carriers include pharmaceutically acceptable carriers such as saline for injection or dextrose for injection.

In further aspect, the invention provides a method for imaging of tissues, comprising administering to a subject to be imaged an effective amount of the composition of the invention. Representative tissues that can be imaged by the method include lymphoid, cardiovascular, liver, kidney, brain, heart, muscle, and gastrointestinal tract tissues, and other tissues accessible by the lymphatic or vascular (blood) systems.

In another aspect, the invention provides a method for delivering a radio-cancer therapeutic agent to a cancer cell, comprising administering to a cancer cell an effective amount of the composition of the invention that includes anion of a radio-isotope.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

FIGS. 2A and 2B compare relaxivity as a function of $Gd^{3+}$ concentration.

FIGS. 3A-3E illustrate time-course coronal images of ventral cavity of M. Nemestrina up to 24 hours after injection of a representative formulation of the invention (Gd-DPTA-PE:mPEG-PE:DSPC).

DETAILED DESCRIPTION OF THE INVENTION

The present invention provides compositions expressing metal ions and methods for using the compositions. In one embodiment, the compositions are lipid nanoparticles that include paramagnetic metal ions and are useful for magnetic resonance imaging. In another embodiment, the compositions are lipid nanoparticles that include ions of radioisotopes and are useful for delivery of radio-cancer therapeutic agents.

In one aspect, the invention provides compositions and methods for magnetic resonance imaging. The compositions and methods enhance gadolinium distribution and accumulation in lymphatics. The invention provides a gadolinium composition (referred to herein as "Gd-DTPA-lipid nanoparticle") that is suitable for both intravenous and subcutaneous administration. Subcutaneous administration allows direct access to lymphatic system. The composition enhances T1 weighted MR signal in the lymph nodes as well as increases the residence time of the contrast agent in the lymphatics. Upon intravenous administration, the composition exhibits at least 100-fold enhancement over soluble Gd-DTPA as a vascular imaging agent and eliminates predominantly through biliary, rather than renal clearance. The composition was shown to significantly increase signal-to-noise ratio by more than 300-fold for MR visualization of lymph nodes in macaques.

The composition of the invention includes a lipid, a polyalkylene-containing lipid, and a lipid-containing metal chelator. In one embodiment, the composition further includes a chelated metal ion.

In one embodiment, the composition of the invention is a chelator- (or metal chelate-) expressing particle. As used herein, the term "expressing" refers to the particle presenting or having available the chelator or chelated metal for activity. As noted above, in one embodiment, the composition of the invention is a lipid nanoparticle having chelated gadolinium ion ($Gd^{+3}$) (e.g., Gd-DTPA-lipid nanoparticle). In the lipid nanoparticle, chelated gadolinium ion is expressed.

The lipid nanoparticles of the invention are biocompatible and are readily administered. The nanoparticles have a diameter of from about 5 nm to about 2 µm. In one embodiment, the nanoparticles have a diameter of from about 10 nm to about 100 µm. In one embodiment, the nanoparticles have a diameter of about 70 nm.

As noted above, the composition of the invention (e.g., lipid nanoparticles) includes a lipid, a polyalkylene-containing lipid, and a lipid-containing metal chelator.

Lipids.

The lipid component of the nanoparticles of the invention comprise the nanoparticle core.

Representative lipids useful in the compositions include phospholipids, sphingolipids, cholesterol and steroid derivatives, bile acids and derivatives, cardilipin, acyl-glycerides and derivatives, glycolipids, acyl-peptides, fatty acids, carbohydrate-based polymers (e.g., cellulose polymers), suitably functionalized silica, lipophilic polymers (e.g., polyanhydrides, polylactate-glycolate), and lipophilic bioploymers (e.g., proteins, sugar polymers).

In one embodiment, the lipid is disteroylamidomethylamine.

In one embodiment, the lipid is a phospholipid. Representative phospholipids include 1,2-distearoyl-sn-glycero-3-phosphocholine (DSPC); dipalmitoyl phosphatidylcholine; dimysristoyl phosphatidyl choline; dioleoyl phosphatidyl choline; trans-esterified phospholipids derived from eggs, soybean, flaxseed, and the like; and phosphatidylcholine substituted with phosphatidyl ethanolamine, phosphatidylglycerol, phosphatidyl serine, and phosphatidic acids. In one embodiment, the phospholipid is 1,2-distearoyl-sn-glycero-3-phosphocholine (DSPC).

Polyalkalene-Containing Lipids.

The polyalkylene-containing lipid component of the nanoparticles of the invention serve as surface hydrating agents.

Representative polyalkylene-containing lipids include polyoxyethylene-containing lipids and polyoxypropylene-containing lipids. In one embodiment, the polyalkylene-containing lipid is a phospholipid functionalized with polyethylene glycol (e.g., PEGylated phospholipid). Suitable PEGylated phospholipids include a polyethylene glycol having a number average molecular weight of from about 500 to about 20,000. In one embodiment, the PEGylated phospholipid is N-(carbonyl-methoxypolyethyleneglycol-2000)-1,2-distearoyl-sn-glycero-3-phosphoethanolamine (mPEG-2000-DSPE) (also referred to herein as "mPEG-DSPE" and "mPEG-PE").

In addition to polyalkylene-containing lipid, in other embodiments, the surface hydrating agent is hydrophilic biomaterials such as a carbohydrate polymer, a polyamine, a polyvinyl pyrrolidone, a poly(aspartate), or a poly(L-amino acid).

Other useful surface hydrating agents include covalent conjugates of polyethoxyl, polymethylene glycol, or propylene glycol and a lipid or other hydrophobic moiety (e.g., long chain hydrocarbon).

The surface hydrating agent is preferably present from about 5 to about 50 mole percent of the composition (i.e., lipid, polyalkylene-containing lipid (surface hydrating agent), and lipid-containing metal chelator).

Lipid-Containing Metal Chelator.

The lipid-containing metal chelator component of the nanoparticles of the invention are expressed on the surface of the nanoparticle and serve to chelate metal ions. Suitable lipid-containing metal chelators include two moieties: (1) a lipid moiety and (2) a metal chelator moiety.

Representative lipid-containing metal chelators include 1,2-distearoyl-sn-glycero-3-phosphoethanolamine-N-diethylenetriaminepentaacetyl (DSPE-DTPA), tetraazacyclododecane, tetraacety(gadodiamide or OMNISCAN)-PE, and lipid-functionalized-[N,N-bis[2-[bis(carboxymethyl)amino]ethyl]-glycinato-(5")](MAGNEVIST).

Representative metal chelators include BOPTA, DO3A, and DOTA chelators.

In one embodiment, the metal chelator includes a PEGylated lipid moiety. Representative PEGylated metal chelators include DSPE-BOPTA, a DSPE-DO3A, and a DSPE-DOTA. In one embodiment, the metal chelator is a PEGylated DTPA (DPTA-PE).

The metal chelator is preferably present from about 5 to about 50 mole percent of the lipid, polyalkylene-containing lipid (surface hydrating agent), and metal chelator.

Chelated Metal Ion.

The compositions of the invention are effective carriers of metal ions. In these embodiments, the composition (e.g., lipid nanoparticles) further includes a chelated metal ion.

For MR applications, useful metal ions include paramagnetic metal ions. Representative paramagnetic metal ions include $Gd^{3+}$, $Cu^{2+}$, $Fe^{3+}$, $Fe^{2+}$, and $Mn^{2+}$ ions.

For other applications such as imaging and therapeutic ion delivery, useful metal ions include ions of radio-isotopes. Representative radio-isotopes include ions of $^{68}Ga$, $^{55}Co$, $^{86}Y$, $^{90}Y$, $^{177}Lu$, and $^{111}In$.

For embodiments that include chelated metal ions, the ratio of metal ion:metal chelator is 0.1-1.0:1.0 (less than or equal to 1:1).

Targeting Agents.

The compositions of the invention can be used to target specific tissues. In these embodiments, the composition (e.g., lipid nanoparticles) further includes a targeting moiety. Representative targeting moieties include proteins, polypeptide, and peptides; antibodies and derivatives (fragments); small molecules; sugars, polysaccharides, and derivatives; and nucleic acids, such as nucleotide polymers (e.g., aptamers), DNAs; and RNAs. Representative targeting moiety targets include cancer cells and virus infected cells.

Lipid Nanoparticle Formulations.

The lipid nanoparticles of the invention can be formulated into compositions for administration. Suitable compositions for administration include a carrier and a plurality of the lipid nanoparticles. Representative carriers include pharmaceutically acceptable carriers, such as saline for injection or dextrose for injection.

The lipid nanoparticle of the invention is not a liposome and does not form liposomes when formulated.

Methods for Tissue Imaging.

In another aspect, the invention provides methods for imaging tissues (e.g., occluded tissues). In one embodiment, the method includes administering to a subject to be imaged a diagnostically effective amount of a composition of the invention. The composition can be administered by a variety of techniques including subcutaneously and intravenously. The method is effective for imaging tissues such as lymphoid, cardiovascular, liver, kidney, brain, heart, muscle, and gastrointestinal tract tissues, and other tissues accessible by the lymphatic or vascular (blood) systems. The method is effective for imaging the tissues above to determine whether the tissues are occluded. For magnetic resonance imaging methods, the composition includes a paramagnetic metal ion (e.g., $Gd^{3+}$).

In general, the effective amount is from about 0.001 to about 5 mmol metal/kg subject. In one embodiment, the effective amount is from about 0.005 to about 0.050 mmol metal/kg subject. In one embodiment, the effective amount is about 0.010 mmol metal/kg subject.

Methods for Radio-Cancer Therapeutic Agent Delivery.

In another aspect, the invention provides methods for delivering a radio-cancer therapeutic agent to a cancer cell. In one embodiment, the method includes administering to a subject in need thereof a therapeutically effective amount of a composition of the invention in which the chelated metal ion is a radio-isotope (e.g., $^{68}Ga$, $^{55}Co$, $^{86}Y$, $^{90}Y$, $^{177}Lu$, and $^{111}In$). The composition can be administered by a variety of techniques including subcutaneously and intravenously. The method is effective for delivery to tissues such as lymphoid, cardiovascular, liver, kidney, brain, heart, muscle, and gastrointestinal tract tissues, and other tissues accessible by the lymphatic or vascular (blood) systems.

The following is a description of the preparation, characterization, and imaging results for representative lipid nanoparticles of the invention.

Figure 1:
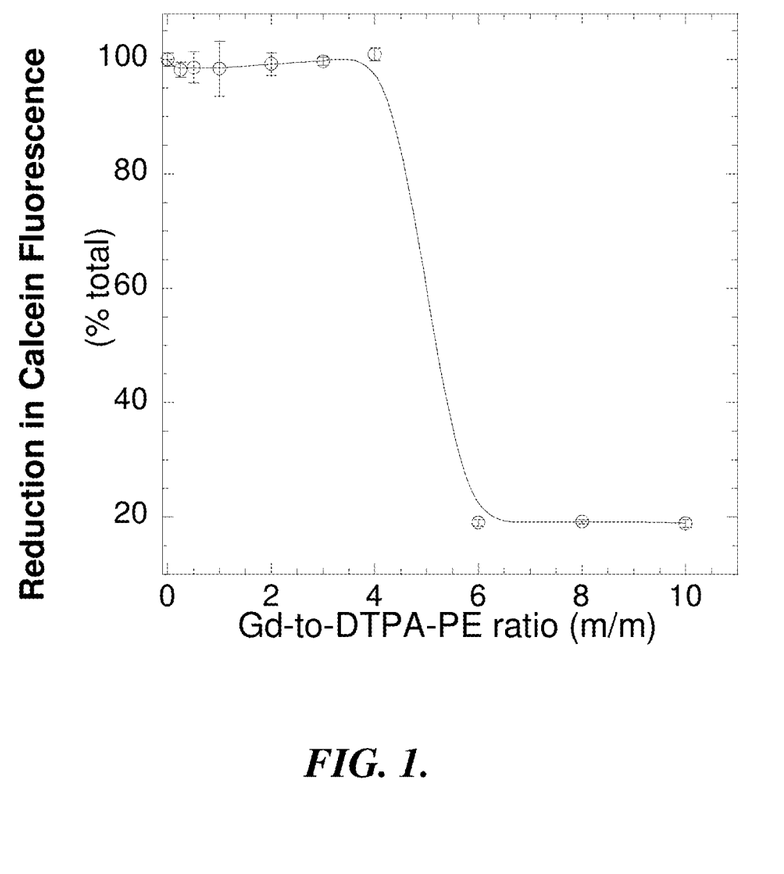
FIG. 1 is a graph illustrating reduction of calcein fluorescence as a function of $Gd^{3+}$:DTPA-PE (m/m) ratio for a representative formulation of the invention. The formulation was incubated with calcein and its fluorescence measured. Free $Gd^{3+}$ binds to calcein and reduces its fluorescence.

Lipid nanoparticles were prepared composed of 10 mole percent of surface-bound DTPA. These lipid nanoparticles contained distearoyl-phosphatidylcholine and PEGylated lipid, mPEG-2000-DSPE. They were allowed to complex with $Gd^{3+}$ (presented as $Gd^{3+}$. CE) at varying $Gd^{3+}$-to-DTPA-PE mole ratios. The presence of free $Gd^{3+}$ in the admixture was determined by the ability of free $Gd^{3+}$ to quench the fluorescence of calcein. With up to a $Gd^{3+}$-to-DTPA-PE mole ratio of 4, no free $Gd^{3+}$ could be detected by the calcein quenching assay. At a 6 or higher $Gd^{3+}$-to-DTPA-PE mole ratio, free or unbound $Gd^{3+}$ was detected (see FIG. 1). To determine the effects of $Gd^{3+}$ on DTPA-expressing lipid nanoparticles, we determined the particle diameter by photon correlation spectroscopy. The diameter of DTPA-expressing lipid nanoparticles was $Gd^{3+}$ concentration dependent. At or below a $Gd^{3+}$-to-DTPA mole ratio of 1, the presence of $Gd^{3+}$ did not influence the diameter of lipid nanoparticles. At a $Gd^{3+}$-to-DTPA mole ratio of 2, the apparent diameter of $Gd^{3+}$-DTPA lipid nanoparticle increases by about 2- to 3-fold, while there is no apparent decrease in the degree of Gd associated with DTPA-lipid nanoparticles (see Table 1). These lipid nanoparticles appeared to be stable as no significant change in diameter was detected over 24 hr at room temperature. Collectively, these data suggest that the ratio of $Gd^{3+}$-to-DTPA influence the degree of $Gd^{3+}$ incorporation into Gd-DTPA lipid nanoparticles and their apparent diameters. At or below $Gd^{3+}$-to-DTPA mole ratio of 2, substantially all $Gd^{3+}$ was associated with lipid nanoparticles. In one embodiment, the $Gd^{3+}$-to-DTPA mole ratio in the composition of the invention is about 1.

Figure 2A:
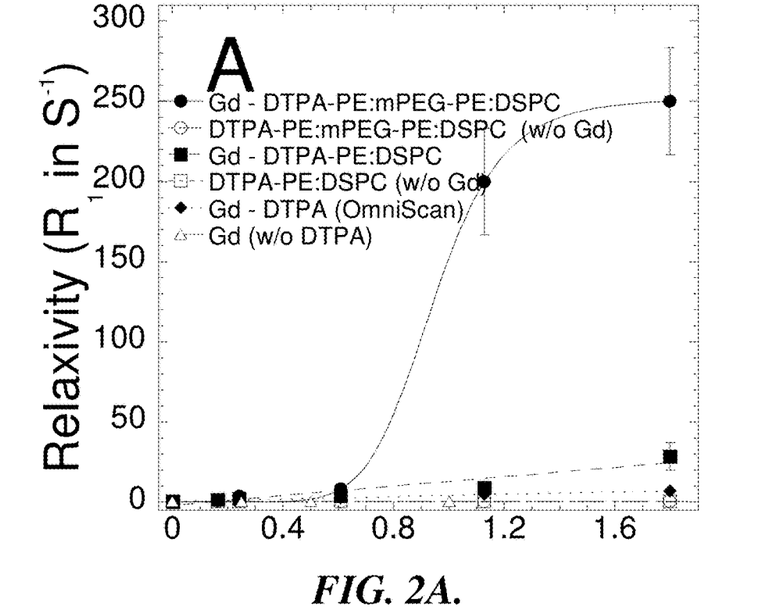
FIG. 2A compares $Gd^{3+}$ dose effect on T1 relaxation rate; $R_1$ (1/T1) values of $Gd^{3+}$ concentrations (μmol/mL) measured in a 1.5T magnetic resonance (MR) scanner using a standard spin-echo sequence for a representative formulation of the invention (Gd-DPTA-PE:mPEG-PE:DSPC) compared to other formulations.

The contrast properties of the $Gd^{3+}$-expressed lipid nanoparticles was determined by comparing the effects of the various $Gd^{3+}$ formulations on the R1 (1/T1) relaxivity of $Gd^{3+}$. Lipid nanoparticles composed of distearoyl-phosphatidylcholine (DSPC) with or without PEGylated lipid (mPEG-2000-DSPE, referred to herein as "mPEG-DSPE" or "mPEG-PE") and fixed $Gd^{3+}$-to-DTPA mole ratio at 1. The T1 and T2 measurements were collected with a 1.5 T MR scanner. A clinically-used Gd-DTPA preparation (OMNISCAN, commercially available from GE Healthcare, Princeton, N.J.) was included as a comparison. As shown in FIG. 2A, the representative composition of the invention, Gd-DTPA lipid nanoparticle containing mPEG-PE (Gd-DTPA-PE:mPEG-PE:DSPC), exhibited significantly higher R1 value than other preparations, including OMNISCAN and lipid nanoparticles that did not contain mPEG. The effects of mPEG on Gd-DTPA lipid nanoparticles are less for T2 measurement (see FIG. 2B). However, the R1 and R2 values for both Gd-DTPA lipid nanoparticle compositions (Gd-DTPA-PE:mPEG-PE:DSPC and Gd-DTPA-PE:DSPC) were significantly higher than that of the soluble Gd-DTPA commercial preparation (OMNISCAN) or free $Gd^{3+}$ in solution (Gd w/o DTPA). To our knowledge the R1 values for Gd-DTPA nanoparticles of the invention are the highest value observed to date including those reported with $Gd^{3+}$-expressed liposome containing PEG. In fact these results were more than 10-fold higher than the data collected with Gd-DTPA liposomes containing egg lectin and cholesterol that express PEG (MW=5000) linked to egg transesterified PE, instead of mPEG linked to DSPE.

Both of the nanoparticle formulations containing $Gd^{3+}$ had higher R1 values than soluble Gd-DTPA. As expected, the DSPC and DSPC plus mPEG-2000-PE control formulations without $Gd^{3+}$ showed no significant effect on relaxivity. The data indicates that the PEG-containing Gd-DTPA-lipid nanoparticles provide a much greater increase in R1 compared to the other formulations. Up to a 100-fold increase in R1 relaxivity was achieved when compared to the commercially available OMNISCAN. The Gd-DTPA nanoparticle formulation without surface PEG (Gd-DTPA-PE:DSPC) also showed higher R1 values than OMNISCAN, but much less than the PEG-containing Gd-DTPA-lipid nanoparticle formulation (Gd-DTPA-PE:mPEG-PE:DSPC) (see FIG. 2A).

Figure 2B:
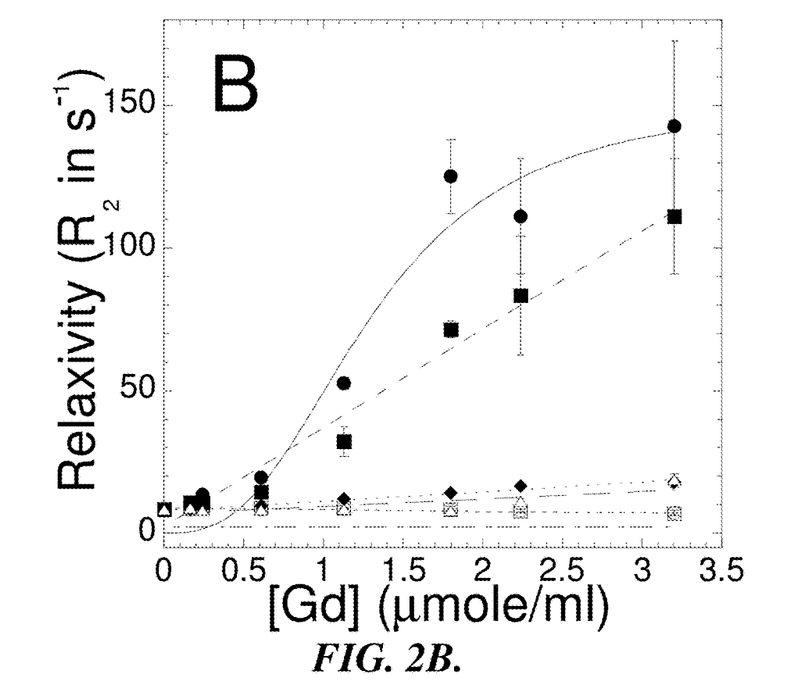
FIG. 2B compares $Gd^{3+}$ dose effect on T2 relaxation rate; $R_2$ (1/T2) values of $Gd^{3+}$ concentrations (μmol/mL) measured in a 1.5T magnetic resonance (MR) scanner using a standard spin-echo sequence for a representative formulation of the invention (Gd-DPTA-PE:mPEG-PE:DSPC) compared to other formulations.

Because positive contrast generated by $Gd^{3+}$ in an MR image is dependant on a low R2/R1 ratio, changes of R2 values were also determined. FIG. 2B demonstrates the effects of the various $Gd^{3+}$ formulations on the R2 (1/T2) relaxivity measurements. Once again the PEGylated Gd-DTPA-lipid nanoparticles (Gd-DTPA-PE:mPEG-PE:DSPC and Gd-DTPA-PE:DSPC) showed a greater increase in R2 compared to the other formulas, however the magnitude of the change was less. The mPEGylated Gd-DTPA-lipid nanoparticles (Gd-DTPA-PE:mPEG-PE:DSPC) showed about eight-fold increase in R2, compared to OMNISCAN. The Gd-DTPA in DSPC (without mPEG) nanoparticle formulation (Gd-DTPA-PE:DSPC) showed a greater increase in R2 than R1, which may limit its effectiveness as a positive contrast agent formulation. The DSPC and DSPC plus mPEG-2000-PE control formulations without $Gd^{3+}$ (DTPA-PE:mPEG-PE:DSPC and DTPA-PE:DSPC) again showed no effect on relaxivity. The relaxivity experiments show that the mPEGylated Gd-DTPA-lipid nanoparticle formulation greatly increases the R1 relaxivity compared to other formulations. However, at high concentrations (greater than 3 μmol/ml), the T1 spillover into T2 becomes significant, leading to an apparent reduction of T1 signal (data not shown). Optimal T1 tissue contrast could be obtained with minimum $Gd^{3+}$ concentration. These data clearly demonstrate much higher contrast "potency" than that provided by the commercial product, OMNISCAN.

The use of the Gd-DTPA lipid nanoparticles containing mPEG-2000-PE (Gd-DTPA-PE:mPEG-PE:DSPC or "Gd-DTPA lipid nanoparticles") for MR imaging studies in primates is described below.

Figure 3A:
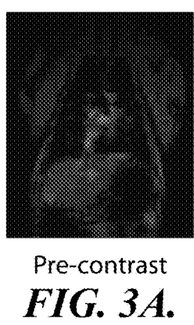
FIGS. 3A-3D are time sequence images of the liver before (FIG. 3A) and after 20 min (FIG. 3B), 6 hr (FIG. 3C), and 24 hr (FIG. 3D) administration.
Figure 3B:
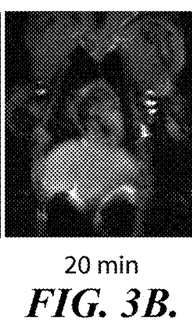
Figure 3C:
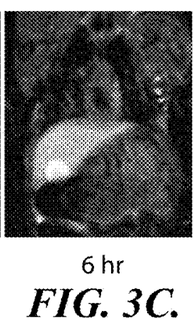
Figure 3D:
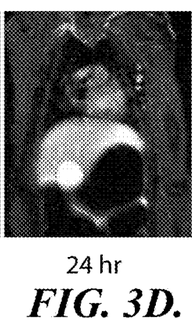
Figure 3E:
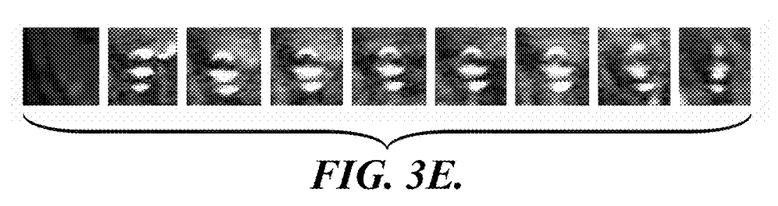
FIG. 3E illustrates time sequence images of lymph nodes. The lymph nodes and liver show high contrast compared to background tissues.
Figure 4A:
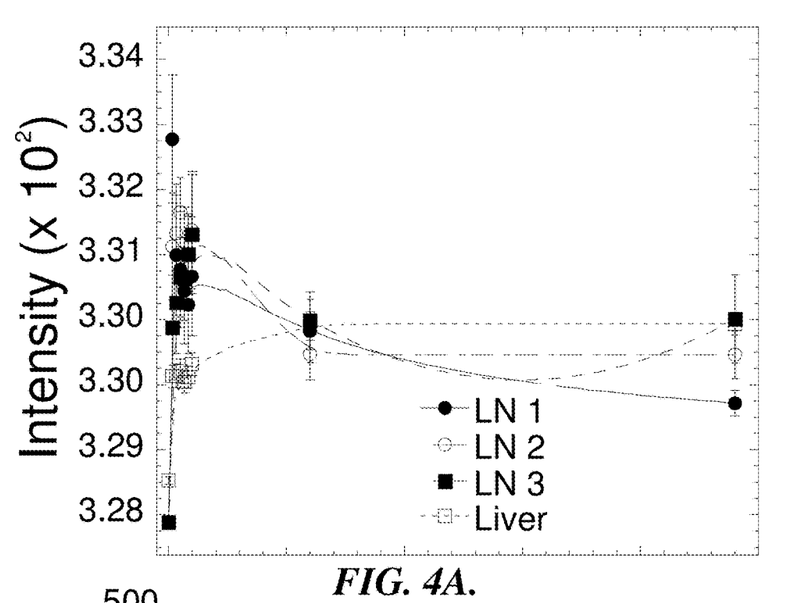
FIG. 4A is a graph comparing MR dynamic contrast enhanced image intensity of the lymph nodes (LN 1, LN 2, and LN3) and liver (Liver) in M. Nemestrina up to 24 hr after subcutaneous injection of 24.4 μmol/kg of a representative formulation of the invention (Gd-DPTA-PE:mPEG-PE:DSPC). Results are for images shown in FIGS. 3A-3D.
Figure 4B:
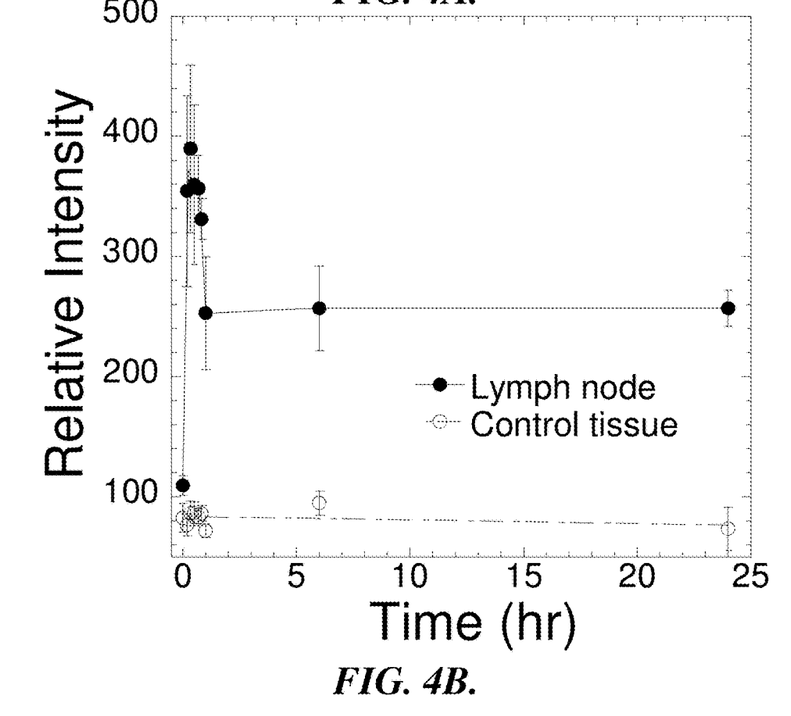
FIG. 4B is a graph comparing the time course of tissue specific MR signal (lymph node) compared to adjacent control tissue.

FIGS. 3A-3D show several coronal MR images of ventral cavity of *M. Nemestrina* both pre-contrast and up to 24 hours following subcutaneous injection of $Gd^{3+}$-DTPA-lipid nanoparticles. The auxiliary lymph nodes are clearly visible with a high degree of intensity enhancement compared to the surrounding tissue (FIG. 3E). The enhancement of the lymph nodes can be seen as early as twenty minutes while lasting up to twenty four hours. FIGS. 4A and 4B show the time course of dynamic contrast enhanced MRI, showing relative intensities of various organs vs. time. This data shows that the $Gd^{3+}$-DTPA-lipid nanoparticles quickly reach the lymph nodes tissue within twenty minutes after injection, and maintain the contrast enhancement for at least twenty four hours. Compared to a low signal that dissipates within 20 min in lymphatic system of animals treated intravenously with soluble Gd-DTPA (OMNISCAN preparations), a single subcutaneous Gd-DTPA lipid nanoparticles dose provided greatly enhanced signal for extended time.

Figure 5A:
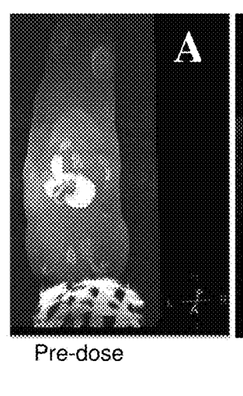
FIGS. 5A-5D are time course MR images of a rat after intravenous injection of a representative formulation of the invention (0.01 mmol/kg Gd-DPTA-PE:mPEG-PE:DSPC): pre-dose (FIG. 5A); 5 min (FIG. 5B); 14 min (FIG. 5C); and 24 hr (FIG. 5D). Contrast enhancement is localized mainly in vasculature and vascularized tissues in lymph nodes at 5 min and 14 min. The arrow in FIG. 5C indicates the beginning of gadolinium elimination into the gastrointestinal tract through the biliary route. By 24 hr (FIG. 5D) most of the contrast agent is eliminated and the residual fraction appears in the intestine.
Figure 5B:
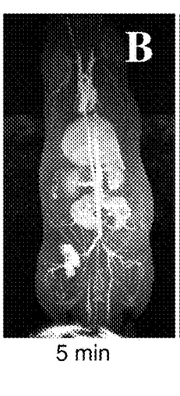
Figure 5C:
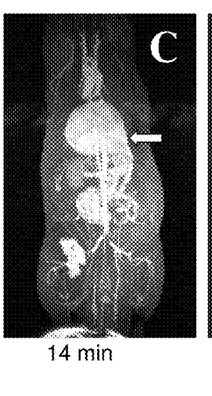
Figure 5D:
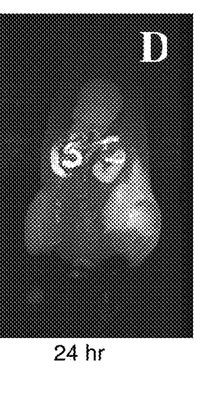
Figure 6A:
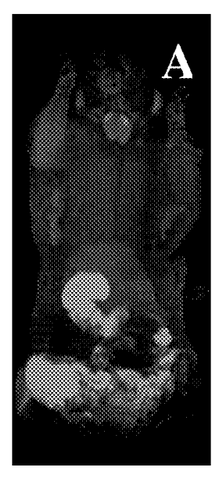
FIGS. 6A-6C are time course MR images of a rat after intravenous injection of a commercially available gadolinium-based contrast agent (0.05 mmol/kg Gd-DPTA, OMNISCAN): pre-dose (FIG. 6A); 5 min (FIG. 6B); and 15 min (FIG. 6C). Contrast enhancement is diffused throughout and does not localize in the vasculature, well-perfused tissues, or the lymph nodes at either 5 min or 15 min. Distribution of contrast media to periphery and extremities is apparent.
Figures 6B, 6C:
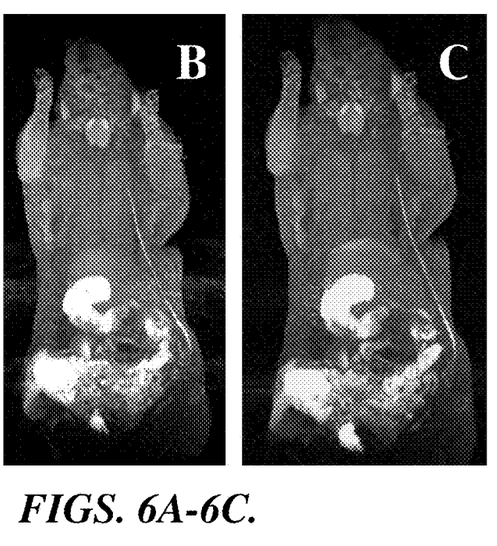
Figures 7A, 7B, 7C, 7D:
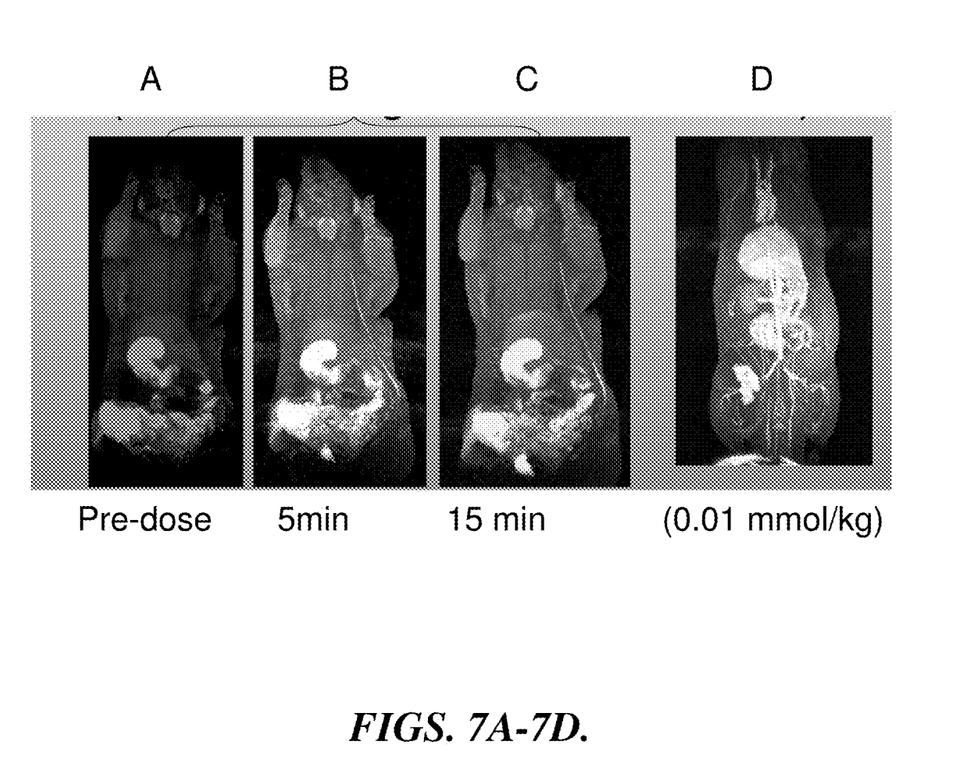
FIGS. 7A-7D compare time course MR images of a rat after intravenous injection of a commercially available gadolinium-based contrast agent (0.05 mmol/kg Gd-DPTA, OMNISCAN, pre-dose (FIG. 7A), 5 min (FIG. 7B), and 15 min (FIG. 7C)) and an MR image of a rat 15 min after administration of a representative formulation of the invention (0.01 mmol/kg Gd-DPTA-PE:mPEG-PE:DSPC (FIG. 7D)).

The MR image enhancing property of the Gd-DTPA-lipid nanoparticles can be used to minimize the IV dose need to produce vascular image enhancement and also reduce renal burden. Administration of 0.01 mmole/kg Gd-DTPA nanoparticles (about ⅕ of current dose for human) in rats produced a high quality MR image with clearly discernable central and peripheral vasculature of rat within 5 min (FIG. 5B). It begins to clear through the bile and gut within 15 min (FIG. 5C), and by the clearance process appeared to complete by 24 hr (FIG. 5D). In contrast, 0.05 mmole soluble Gd-DTPA (OMNISCAN) produce diffuse contrast localization with no vascular definition; it also appeared to distribute to periphery an extremities (FIG. 6A). In a limited dose-response study, only about to 10-20-fold lower dose of the Gd-DTPA-lipid nanoparticles, compared to current Gd-DTPA formulation, is needed in rat to produce equivalent or better definition of contrast enhanced MR images in rats. The 0.0025 mmole/kg Gd in DTPA-lipid nanoparticles produce equivalent image quality of 0.05 mmole/kg Gd-DTPA (OMNISCAN) preparation. Therefore, the Gd-DTPA-lipid nanoparticles may overcome challenges in the clinical use with currently approve Gd contrast agents due to renal insufficiency and neurotoxicity.

The PEGylated lipid nanoparticles of the invention having surface-bound gadolinium ion exhibited a great improvement over other preparations in contrast enhanced MR lymphography and vascular imaging. These lipid nanoparticles showed high degree of accumulation in the lymph nodes after subcutaneous injection. The contrast enhancement in lymphoid tissue begins within 20 minutes of injection and is maintained for 24 hours. When given intravenously this agent produced high quality images of vasculature in much higher sensitivity than the current agents. Intravenously administered lipid nanoparticles are cleared almost exclusively through biliary route and appeared to complete within 24 hr. Surface modification by adding mPEG in lipid nanoparticles increased the MR signal of $Gd^{3+}$ through coordination of water molecules. This leads to a much higher R1 relaxivity and lymph node image enhancement. The lipid nanoparticle formulation may allow using a low dose to achieve a high signal-to-noise MR contrast ratio for increasing the metastatic nodal discrimination and allowing for a much wider time frame for imaging. The potentially lower dose and more favorable elimination route of $Gd^{3+}$ needed for MR contrast could provide higher safety margin.

Figures 8A, 8B, 8C, 8D, 8E, 8F:
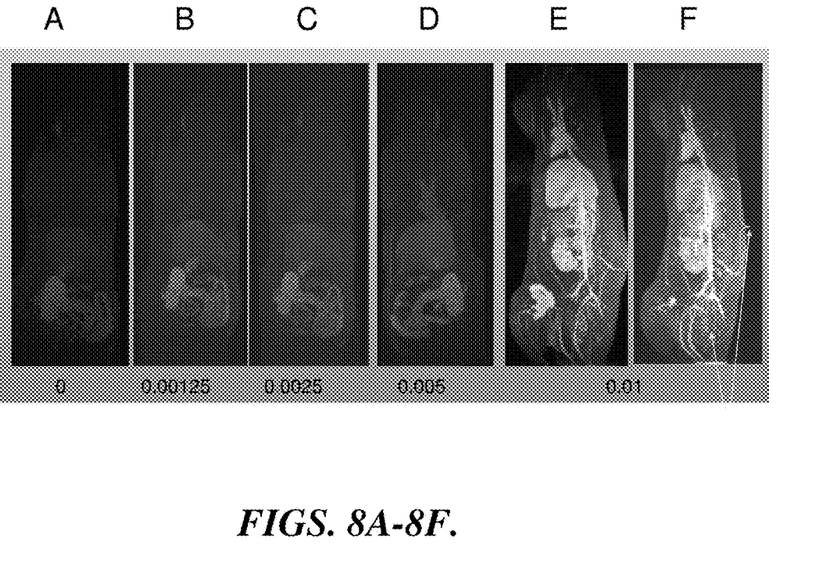
FIGS. 8A-8F compare dose response MR images of a rat after intravenous injection of a representative formulation of the invention (Gd-DPTA-PE:mPEG-PE:DSPC): 0.0 mmol/kg (FIG. 8A); 0.00125 mmol/kg (FIG. 8B); 0.0025 mmol/kg (FIG. 8C); 0.005 mmol/kg (FIG. 8D); and 0.010 mmol/kg (FIG. 8E and FIG. 8F). Lymph nodes are clearly apparent in FIG. 8F.

The formulations of the invention provide effective contrast at relatively low dose compared to currently available and approved contrast agents. FIGS. 8A-8F compare dose response MR images of a rat after intravenous injection of a representative formulation of the invention (Gd-DPTA-PE:mPEG-PE:DSPC): 0.0 mmol/kg (FIG. 8A); 0.00125 mmol/kg (FIG. 8B); 0.0025 mmol/kg (FIG. 8C); 0.005 mmol/kg (FIG. 8D); and 0.010 mmol/kg (FIG. 8E and FIG. 8F). Lymph nodes are clearly apparent in FIG. 8F.

Figure 9A:
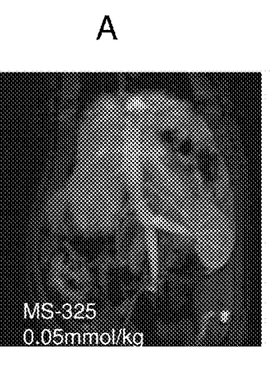
FIGS. 9A-9C compare MR images of rats after intravenous injection of two commercially available gadolinium-based contrast agents (0.05 mmol/kg MS-325, FIG. 9A; 0.05 mmol/kg MAGNEVIST Gd-DPTA, FIG. 9B) and a representative formulation of the invention (0.01 mmol/kg Gd- DPTA-PE:mPEG-PE:DSPC, FIG. 9C). Images were acquired near peak enhancement, about 1 to 2 min after administration.
Figure 9B:
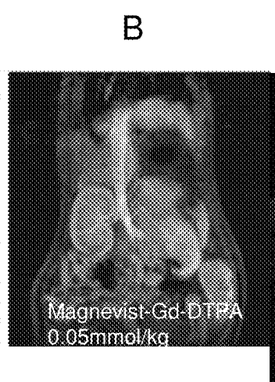
Figure 9C:
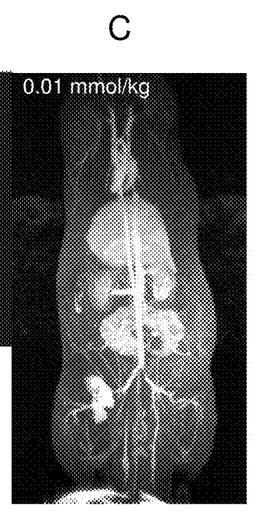

As noted above, the formulations of the invention offer advantages over currently available and approved contrast agents. FIGS. 9A-9C compare MR images of rats after intravenous injection of two commercially available gadolinium-based contrast agents (0.05 mmol/kg MS-325, EPIX Pharmaceuticals, Inc., Cambridge, Mass., FIG. 9A; and 0.05 mmol/kg MAGNEVIST Gd-DPTA, Bayer HealthCare Pharmaceuticals, FIG. 9B) and a representative formulation of the invention (0.01 mmol/kg Gd-DPTA-PE:mPEG-PE:DSPC, FIG. 9C). Images were acquired near peak enhancement, about 1 to 2 min after administration. As can be seen from the images, the representative formulation of the invention demonstrates significantly greater contrast than the currently available agents.

Figure 10:
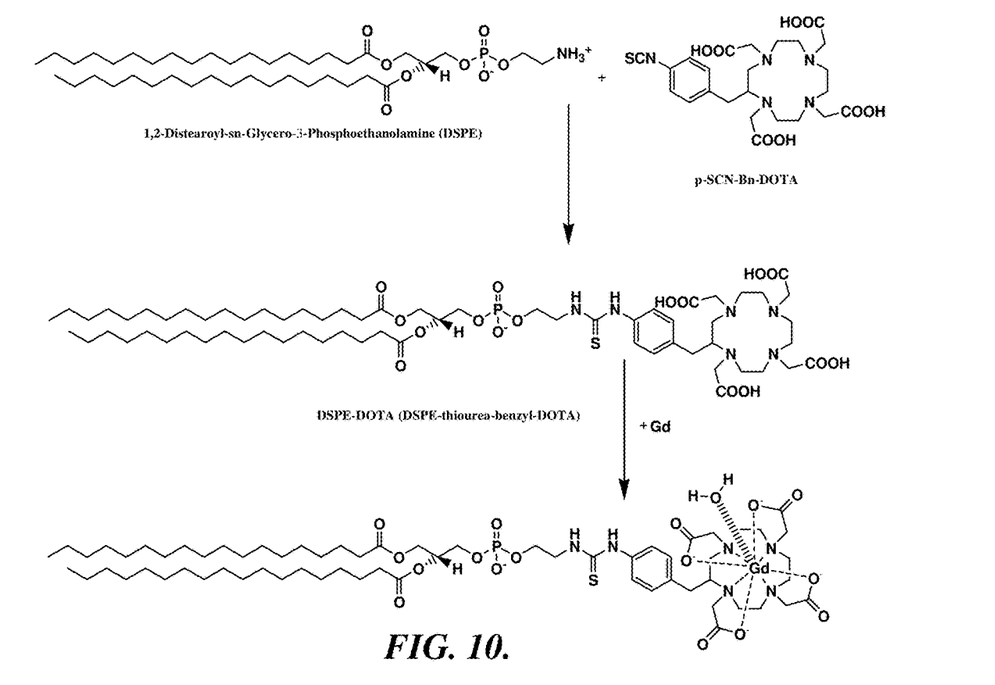
FIG. 10 is a schematic illustration of the preparation of a representative lipid-containing gadolinium chelate: DSPE-DOTA-Gd.
Figure 11:
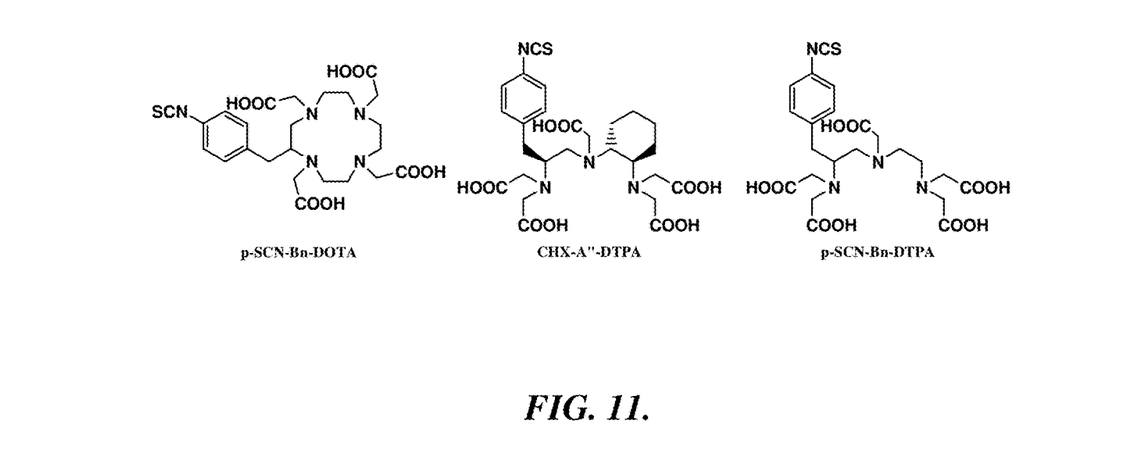
FIG. 11 illustrates three metal chelators useful for preparing representative lipid-containing chelates: p-SCN-Bn-DOTA; CHX-A"-DTPA; and p-SCN-Bn-DTPA.

FIG. 10 is a synthetic scheme for preparing a representative Gd complexes useful in the invention (DSPE-DOTA-Gd) by reacting DSPE with p-SCN-Bn-DOTA followed by Gd metallation. FIG. 11 illustrates three representative chelating agents (isothiocyanates, —N=C=S or —NCS)

(p-SCN-Bn-DOTA, CHX-A"-DTPA, and p-SCN-Bn-DTPA) that are reactive toward phospholipids and useful in the invention.

Figure 12:
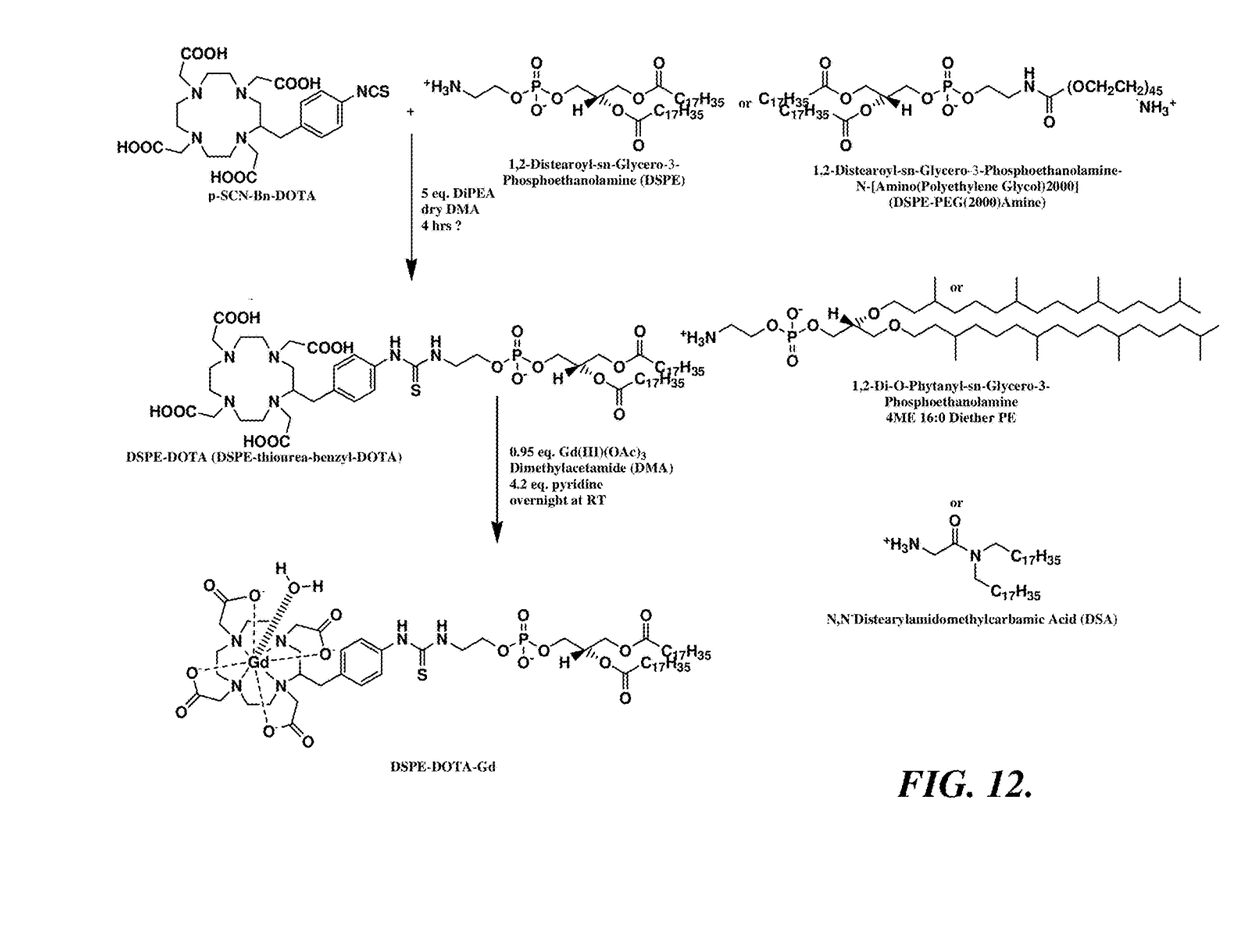
FIG. 12 is a schematic illustration of the preparation of representative lipid-containing gadolinium chelates.

FIG. 12 illustrates four representative lipophilic compounds (DSA, Diether PE, DSPE-PEG(2000) Amine, and DSPE) and a synthetic scheme for preparing a representative Gd complex useful in the invention (DSPE-DOTA-Gd) by reacting DSPE with p-SCN-Bn-DOTA followed by Gd metallation. Lipid-containing metal chelators useful in the invention are readily prepared as shown in FIGS. 10 and 12. Suitably reactive metal chelators (e.g., isothiocyanate-functionalized metal chelators, see FIG. 11) are reacted with lipid compounds containing suitably reactive groups (e.g., amino groups in DSPE, DSPE-PEG(2000) Amine, Diether PE, DSA, see FIGS. 10 and 12) to provide lipid-containing metal chelators in which the lipid moiety is covalently coupled to the metal chelator. For isothiocyanate-functionalized metal chelators and reactive amine-containing lipids, the product lipid-containing metal chelator includes a thiourea (—NH—C(=S)—NH—) linkage coupling the lipid to the chelator. It will be appreciated that other suitably reactive metal chelators (e.g., isocyanate) and lipid compounds containing suitably reactive groups (e.g., alcohol) can provide lipid-containing metal chelators useful in the invention. Metallation of the chelators provides the metal ion-containing compounds.

TABLE 1

Effects of the $Gd^{3+}$ to DTPA mole ratio on particle size and stability of $Gd^{3+}$-lipid nanoparticles[a].

| $Gd^{3+}$:DTPA (m/m) ratio[b] | Particle diameter (nm)[c] | | Free or unbound $Gd^{3+}$[d] |
|---|---|---|---|
| | After preparation | At 24 hr | |
| 0 | 52 ± 0.05 | 65 ± 0.3 | — |
| 0.5 | 46 ± 0.09 | 49 ± 0.07 | 1.4 ± 2.7% |
| 1 | 41 ± 0.1 | 48 ± 0.1 | 1.6 ± 4.8% |
| 2 | 137 ± 0.15 | 145 ± 0.2 | 0.8 ± 2.0% |

[a]DTPA is expressed on lipid nanoparticles composed of DSPC, mPEG-PE and DTPA-PE (8:1:0.9 mole ratio, as described in Example 1.
[b]The nanoparticles were exposed to $GdCl_3$ at indicated DTPA to $Gd^{3+}$ mole ratio.
[c]The diameter of DTPA expressed nanoparticles were measured by photon correlation spectroscopy and data expressed were mean ± SD of quadruplicate samples at indicated time points.
[d]The presence of unbound or free $Gd^{3+}$ was estimated with calcein fluorescence quenching assay.

The following examples are provided for the purpose of illustration, not limiting, the invention.

EXAMPLES

Example 1

Materials and Methods

Lipid Nanoparticle Preparation.

1,2-distearoyl-sn-glycero-3-phosphocholine (DSPC, Avanti Polar Lipids, AL), N-(carbonyl-methoxypolyethyleneglycol-2000)-1,2-distearoyl-sn-glycero-3-phosoethanolamine (mPEG-2000-DSPE, Genzyme, MA), and 1,2-di stearoyl-sn-glycero-3-phophoethanolamine-N-DTPA (DSPE-DTPA, Avanti Polar Lipids, AL) were combined in chloroform (DSPC:mPEG-DSPE:DSPE-DTPA) in a ratio of 8:2:1 and dried into a thin film under nitrogen and then under high vacuum overnight. The mPEG-DSPE containing PEG polymers of various molecular weights (or chain lengths) are also purchased from Genzyme, MA. At this point phosphate buffered saline (PBS, pH 7.4) was added to the film and sonicated in a bath-type sonicator (Laboratory Supplies Company, New York). The vesicle diameter, as measured by dynamic light scattering using a Malvern Zetasizer 5000 photon correlation spectroscopy (Malvern Instruments, PA), was 50 nm. The nanoparticles in suspension were mixed with gadolinium (III) chloride hexahydrate (Aldrich, St Louis, Mo.) for 20 minutes at indicated mole ratio to form Gd-DTPA-lipid nanoparticles. To determine the unbound $Gd^{3+}$, the nanoparticles were incubated with calcein (0.5 M) (Sigma, St Louis, Mo.) in PBS, pH 7.4, and the fluorescence was measured at 485/535 nm using a Victor3V 1420 multilabel counter (PerkinElmer, Waltham, Mass.). Free ionic $Gd^{3+}$ quenches calcein fluorescence in $[Gd^{3+}]$ dependent manner. To determine the final Gd concentration, elemental Gd mass was determined using the inductively coupled plasma atomic emission spectrometry. The particles along with control particles without $Gd^{3+}$ were used in the studies described herein.

Relaxivity Studies.

Dilutions of Gd-DTPA-lipid nanoparticles were prepared with $Gd^{3+}$ concentrations between 0-5 μmol/ml. For comparison several samples were prepared from commercial agents such as OMNISCAN (Gd-DTPA-BMA) with $Gd^{3+}$ concentrations from 0-5 μmol/ml. The relaxation time T1 was measured using the standard spin-echo sequence on a 1.5T MR scanner with a volume head coil as RF receiver. For T1 measurements, TE was fixed to 9 ms and seven TR were 133, 200, 300, 500, 750, 1000 and 2000 ms, respectively. For T2 measurements, TR was fixed to 2000 ms and four TE were 15, 30, 45, and 60 ms, respectively. The imaging intensities were fitted to obtain the corresponding T1 and T2 values, which were plotted versus $Gd^{3+}$ concentration.

Primate Lymphatic MRI Study.

In vivo imaging of the lymph nodes using Gd-DTPA-lipid nanoparticles for dynamic contrast enhanced (DCE) MRI was performed in a 1.5T MR scanner. The pigtailed macaque (*M. Nemestrina*) was anesthetized with inhaled isofluorane (1-2%) and closely monitored during the experiments. A pre-contrast image of the primate was recorded to determine proper lymph node location and fine-tune the imaging parameters. The animal was removed from the MR scanner and injected subcutaneously at four sites. Each injection site received 2, 5, 5, and 8.5 mL, respectively of 6.1 μmol/ml Gd-DTPA-lipid nanoparticles to allow probing of dose effects and contrast diffusion from injection sites. The total dose of Gd is estimated to be 24.4 μmol/kg for the primate studies. The images were recorded on a Signa 1.5T Scanner using a surface coil 12×12 $inch^2$. A standard spin-echo imaging sequence was used with TR=500 ms, TE=15 ms, slice thickness of 3 mm, 21 slices, slice gap=0.5 mm, FOV (field of view)=320×320 $mm^2$, matrix size=512×512, which gives an in-plane resolution of 0.63×0.63 $mm^2$ and a temporal resolution is 3.1 min.

Rat Vascular MRI Study.

In vivo imaging of the rat using Gd-DTPA-lipid nanoparticles for dynamic contrast enhanced (DCE) MRI was performed in a 3.0T MR scanner. The rats (SD) was anesthetized with inhaled isofluorane (1-2%) and closely monitored during the experiments. A pre-contrast image of the rat was recorded to determine proper location, orientation and fine-tune the imaging parameters. The animal was removed from the MR scanner and injected with 400 L of indicated Gd contrast media through femoral vein. The images were recorded on a Signa 1.5T Scanner using a surface coil 12×12 inch. A standard spin-echo imaging sequence was used with TR=500 ms, TE=15 ms, slice thickness of 3 mm, 21 slices, slice gap=0.5 mm, FOV (field of view)=320×320 $mm^2$, matrix size=512×512, which gives an in-plane resolution of 0.63×0.63 mm$^2$ and a temporal resolution is 3.1 min.

While the preferred embodiment of the invention has been illustrated and described, it will be appreciated that various changes can be made therein without departing from the spirit and scope of the invention.

The invention claimed is:

1. A nanoparticle, comprising:
(a) a phospholipid selected from distearoyl-phosphocholine (DSPC) or dipalmitoyl sphingomyelin (DPSP);
(b) |N-(carbonyl-methoxypolyethyleneglycol)-1,2-distearoyl-sn-glycero-3-phosphoethanolamine (mPEG-DSPE); and
(c) 1,2-distearoyl-sn-glycero-3-phosphoethanolamine-N-diethylenetriaminepenta-acetyl (DSPE-DTPA) with a chelated Gd$^{3+}$ ion, wherein the nanoparticle is not a liposome, and wherein the nanoparticle has a T1 relaxivity constant ($r_1$) of at least about 133 sec$^{-1}$ mM$^{-1}$ as determined by a magnetic resonance (MR) scanner;
wherein the mPEG-DSPE is present in the amount from about 5 to about 20 mole percent of the combined phospholipid, the mPEG-DSPE, and DSPE-DTPA, and
wherein the phospholipid:mPEG-DSPE:DSPE-DTPA ratio is from 8:1:0.9 to 8:2:1.

2. The nanoparticle of claim 1, wherein the N-(carbonyl-methoxypolyethyleneglycol)-1,2-distearoyl-sn-glycero-3-phosphoethanolamine (mPEG-DSPE) is N-(carbonyl-methoxypolyethyleneglycol-2000)-1,2-distearoyl-sn-glycero-3-phosphoethanolamine (mPEG-2000-DSPE).

3. The nanoparticle of claim 1, further comprising a targeting moiety.

4. The nanoparticle of claim 3, wherein the targeting moiety is selected from the group consisting of a protein, a polypeptide, a peptide, an antibody or fragment thereof, a small molecule, a sugar or polysaccharide or derivative thereof, and a nucleic acid.

5. A composition, comprising a carrier and a plurality of the nanoparticles of claim 1.

6. The nanoparticle of claim 1, wherein the nanoparticle comprises 1,2-distearoyl-sn-glycero-3-phosphocholine (DSPC), and N-(carbonyl-methoxypolyethyleneglycol-2000)-1,2-distearoyl-sn-glycero-3 phosphoethanolamine (mPEG-2000-DSPE).

7. The nanoparticle of claim 1, wherein the nanoparticle does not have a solid core structure.

* * * * *